(12) United States Patent
Aminpour

(10) Patent No.: US 9,114,097 B1
(45) Date of Patent: Aug. 25, 2015

(54) COMPOSITION OF NATURAL TOOTHPASTE

(71) Applicant: Babak Aminpour, Riverside, CA (US)

(72) Inventor: Babak Aminpour, Riverside, CA (US)

( * ) Notice: Subject to any disclaimer, the term of this patent is extended or adjusted under 35 U.S.C. 154(b) by 0 days.

(21) Appl. No.: 14/587,454

(22) Filed: Dec. 31, 2014

(51) Int. Cl.
*A61K 8/97* (2006.01)
*A61K 8/365* (2006.01)
*A61K 8/19* (2006.01)
*A61K 8/34* (2006.01)
*A61K 8/92* (2006.01)
*A61K 33/10* (2006.01)
*A61K 6/00* (2006.01)
*A61K 8/00* (2006.01)
*A61Q 11/00* (2006.01)

(52) U.S. Cl.
CPC ... *A61K 8/97* (2013.01); *A61K 8/19* (2013.01); *A61K 8/345* (2013.01); *A61K 8/365* (2013.01); *A61K 8/922* (2013.01); *A61Q 11/00* (2013.01); *A61K 2800/31* (2013.01)

(58) Field of Classification Search
USPC .................................................. 424/50, 52
See application file for complete search history.

(56) References Cited

U.S. PATENT DOCUMENTS

| 5,004,596 | A | * | 4/1991 | Cocherell et al. | 424/52 |
| 5,925,335 | A | * | 7/1999 | Shuch et al. | 424/49 |
| 2007/0098650 | A1 | * | 5/2007 | Miller et al. | 424/50 |

* cited by examiner

*Primary Examiner* — Walter Webb
(74) *Attorney, Agent, or Firm* — Omni Legal Group; Omid E. Khalifeh

(57) ABSTRACT

A composition of natural toothpaste is provided which promotes the healthful effects of whitening teeth, freshening breath, sanitizing the mouth, and removing plaque and other buildup from enamel while avoiding risks associated with traditional artificial and/or synthetic ingredients. More particularly, coconut oil is provided to reduce bacteria in the mouth, whiten teeth, and freshen breath in combination with stevia and other ingredients as antioxidants, flavor enhancers, and/or anti-inflammatory agents.

4 Claims, No Drawings

COMPOSITION OF NATURAL TOOTHPASTE

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

The following is a tabulation of some prior art that presently appears relevant:

| U.S. Patents | | | |
|---|---|---|---|
| Patent Number | Kind Code | Issue Date | Patentee |
| 6,485,711 | B1 | Mar. 21, 2002 | Olmstead |

| U.S. Patent Application Publications | | | |
|---|---|---|---|
| Publ. Number | Kind Code | Publ. Date | Applicant |
| 2012/0201764 | A1 | Aug. 9, 2012 | Day |

| Foreign Patent Documents | | | |
|---|---|---|---|
| Country Code | Publ. Number | Kind Code | Publ. Date |
| CN | 103451017 | A | Dec. 18, 2013 |
| CN | 102579305 | B | Oct. 9, 2013 |

NONPATENT LITERATURE DOCUMENTS

None found.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

BACKGROUND

1. Technical Field

The disclosed subject matter relates generally to a composition of toothpaste, and more particularly, to a toothpaste having all natural and even organic ingredients.

2. Discussion of the Related Art

It is well known that oral hygiene is essential for preserving teeth and also preventing various diseases related to bacteria and plaque buildup in the mouth. A number of formulations for toothpaste that whitens and cleans the surface of the teeth, freshens breath, and sanitizes the mouth, separately or in combination, have been proposed as a result.

Many of these proposals, however, include synthetic detergents as surfactants, such as sodium lauryl sulfate (sls), and additional chemicals, such as natural or synthetic fluoride. Although these ingredients, commonly found in products offered by popular Crest® and Colgate® brands, may efficiently remove grime and protect enamel, they have been known in some instances to cause ulcers in the mouth and may pose other risks when ingested. Furthermore, some people adhere to strict dietary and lifestyle habits, which encourage them to minimize their use of artificial and synthetic products. Thus, it is desirable to avoid such ingredients.

Some proposed solutions to the problem, include, for example, traditional toothpaste alternatives available on the market include those offered by Tom's of Maine® and The Honest Co®. With respect to the former, fluoride-free and sls-free formulations have been provided. However, they include filler ingredient titanium dioxide, commonly used as a pigment, which many consumers avoid out of fear that the ingredient can lead to problems with immune function in the body. With respect to the latter, salt, and other ingredients that may be irritating to the mouth and gums, are included in the composition.

Although various solutions have been proposed, none combine the characteristics of the present invention. Thus, there is a need for a natural, and preferably organic, toothpaste having whitening, antibacterial, and anti-inflammatory properties. The composition of the present invention effectuates those needs.

SUMMARY

The present disclosure is directed to a composition for toothpaste comprising a mixture of natural ingredients. In a preferred embodiment, the natural ingredients may be organic.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

It is a primary object of this disclosure to provide natural toothpaste, which promotes the same desirable whitening, freshening, sanitizing, and anti-inflammatory results of traditional toothpaste, while avoiding risks associated with artificial and/or synthetic ingredients.

In accordance with one embodiment, the composition includes about between about 10% to about 45% by weight coconut oil as an anti bacterial and tooth whitening agent.

In an embodiment, the composition further comprises baking soda as an abrasive, which may aid in removing plaque and other buildup from the surface of the teeth.

In yet another embodiment, the composition may further comprise stevia as an antioxidant, gingival anti-inflammatory, and flavor enhancer.

In still another embodiment, the composition may further include glycerin, such as vegetable glycerin, as a moisturizing agent.

In another embodiment, the composition may further include natural flavoring, such as peppermint extract.

One or more of the above-disclosed embodiments, in addition to certain alternatives, are provided in further detail below. The disclosed subject matter is not, however, limited to any particular embodiment disclosed.

ADVANTAGES

Several advantages of one or more aspects are to provide a natural toothpaste that:
(a) whitens teeth;
(b) lowers gingival inflammation in the mouth;
(c) reduces bacteria in the mouth;
(d) includes antioxidants;
(e) freshens breath;
(f) avoids artificial and/or synthetic ingredients;
(g) improves oral health; and
(h) has a pleasant taste.

These and other advantages of one or more aspects will become apparent from consideration of the ensuing description and accompanying examples. Although the description above contains many specifics, these should not be construed as limiting the scope of the embodiments but as merely providing illustrations of some of several embodiments. Thus the scope of the embodiments should be determined by the claims that the appended and their legal equivalents, rather than by the examples given.

The description of the invention which follows, together with the accompanying examples should not be construed as limiting the invention to the examples shown and described, because those skilled in the art to which this invention pertains will be able to devise other forms thereof within the ambit of the appended claims.

DETAILED DESCRIPTION

Illustrative embodiments of the invention are described below. The showings are for purposes of illustrating preferred embodiments and not for purposes of limiting the same. The following explanation provides specific details for a thorough understanding of an enabling description for these embodiments One skilled in the art will understand that the invention may be practiced without such details. In other instances, well-known structures and functions have not been shown or described in detail to avoid unnecessarily obscuring the description of the embodiments.

In an embodiment, the composition for natural toothpaste includes ingredients, which have only been processed to the extent necessary to make them safe for human consumption. In the preferred embodiment, the ingredients are organic.

The composition comprises about between about 9.8 to about 44.9% by weight of coconut oil. In an embodiment, the composition may comprise between about 22.1 to about 30.0% of coconut oil. In some embodiments coconut oil exhibits antibacterial properties, whitens teeth, freshens breath, lowers gingival inflammation, and generally improves oral health. In addition, the composition may comprise about 9.8 to about 19.9% by weight of stevia. In some embodiments, stevia may be provided as an anti-inflammatory agent and antioxidant. It may also improve the overall taste of the composition, so that humans will be more willing to regularly use the composition in line with hygienic recommendations.

Both coconut oil and stevia may further reduce the risk of dental decay.

In an embodiment, the composition may further comprise about 20.0 to about 44.9% by weight of baking soda. In another embodiment, the composition comprises about 33.1 to about 42.9% by weight of baking soda. In particular, baking soda may provide the benefits of acid neutralization due to its being a chemically weak base. Moreover, its abrasive properties may further provide the benefits of tooth-whitening, stain removal, and plaque removal.

In an embodiment, the composition may further comprise a moisturizing agent such as glycerin. In a preferred embodiment, the glycerin may be a vegetable glycerin derived from any vegetable fat through hydrolysis. More particularly, the composition may comprise about 0.1% to about 9.9% by weight of vegetable glycerin. The moisturizing agent may be included to preserve the combined ingredients of the natural toothpaste. The moisturizing agent may also act as an emulsifier, which aids even application of the natural toothpaste to the teeth.

The composition for natural toothpaste may also include an additional natural flavoring such as herbal, floral, or fruit extract. In a preferred embodiment, the composition comprises 0.1% to about 9.9% by weight of peppermint, spearmint, or other herbal mint extract. In one embodiment, peppermint extract may relieve gum pain, freshen breath, and prevent the formation of dental cavities.

In a preferred embodiment, water is avoided as an ingredient. This may ensure that the healthful benefits of ingredients comprising the natural toothpaste are not diluted.

EXAMPLES OF THE PREFERRED EMBODIMENT

In order to more fully teach what the Applicant regards as his invention, the following example is given. It should be understood that the formulations set forth in the Example is not to be construed as limiting of the scope of the invention, except so far as they yield natural toothpaste having the desired properties and characteristics.

Natural toothpastes have been proposed in the past. By way of example, the following chart illustrates a formulation of the same with the percentages given by weight of the toothpaste.

| Ingredient | Percentage |
|---|---|
| Vegetable glycerin | 46.570 |
| Calcium carbonate | 26.000 |
| Water | 9.370 |
| Aloe vera juice | 6.000 |
| Fumed silica | 1.650 |
| Hydrated silica | 4.300 |
| Baking soda | 2.200 |
| Quillaja | 1.000 |
| Carrageenan | .715 |
| Peppermint oil | .820 |
| Manuka oil | .600 |
| Grapefruit seed extract | .375 |
| Green papaya extract | .400 |

The following ingredients are an example of Applicant's invention with the percentages being given by weight of the toothpaste:

| Ingredient | Percentage |
|---|---|
| Coconut oil | 25.8 |
| Stevia | 17.5 |
| Baking soda | 42.7 |
| Vegetable glycerin | 7.00 |
| Peppermint extract | 7.00 |
| TOTAL: | 100.0% |

CONCLUSIONS, RAMIFICATIONS, AND SCOPE

While certain embodiments of the invention have been illustrated and described, various modifications are contemplated and can be made without departing from the spirit and scope of the invention. For example, it is contemplated that various natural flavorings may be included or substituted in the composition. In one contemplated embodiment, anise oil may be the natural flavoring. In other embodiments, other herb extracts may be used instead. Accordingly, it is intended that the invention not be limited, except as by the appended claim(s).

The teachings disclosed herein may be applied to other compositions, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the compositions and concepts of the various references described above to provide yet further embodiments of the invention.

Particular terminology used when describing certain features or aspects of the invention should not be taken to imply that the terminology is being refined herein to be restricted to any specific characteristics, features, or aspects of the ingredients with which that terminology is associated. In general, the terms used in the following claims should not be constructed to limit the ingredients of the natural toothpaste disclosed in the specification unless the above description section explicitly define such terms. Accordingly, the actual scope encompasses not only the disclosed embodiments, but also all equivalent ways of composing or implementing the disclosed ingredients. The above description of embodiments of the natural toothpaste is not intended to be exhaustive or limited to the precise form disclosed above or to a particular field of usage. While specific embodiments of, and examples for, the natural toothpaste and ingredients thereof are described above for illustrative purposes, various equivalent modifications are possible for which those skilled in the relevant art will recognize.

While certain aspects of the natural toothpaste disclosed are presented below in particular claim forms, various aspects of the method and system are contemplated in any number of claim forms. Thus, the inventor reserves the right to add additional claims after filing the application to pursue such additional claim forms for other aspects of the composition for natural toothpaste.

What is claimed is:

1. Natural toothpaste comprising:
   27 wt. % coconut oil
   16.66 wt. % stevia;
   41.66 wt. % baking soda;
   6.94 wt. % vegetable glycerin; and
   6.94 wt. % peppermint extract.

2. The toothpaste of claim 1, wherein the coconut oil is organic.

3. The toothpaste of claim 1, wherein the vegetable glycerin is organic.

4. The toothpaste of claim 1, wherein the peppermint extract is organic.

* * * * *